United States Patent
Wagner et al.

(10) Patent No.: US 10,137,400 B2
(45) Date of Patent: Nov. 27, 2018

(54) RECYCLING PROCESS FOR ADSORBER REGENERATION

(71) Applicant: BASF SE, Ludwigshafen (DE)

(72) Inventors: Hans-Guenter Wagner, Neuleiningen (DE); Christoph Bayer, Nuremberg (DE); Lothar Karrer, Pfungstadt (DE); Heinz Ruetter, Xanten (DE); Patrik Pietz, Shanghai (CN); Sven Crone, Limburgerhof (DE); Markus Eggersmann, Speyer (DE); Kam Wing Wong, Tsuen Wan (CN)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/517,286

(22) PCT Filed: Oct. 9, 2014

(86) PCT No.: PCT/CN2014/088225
§ 371 (c)(1),
(2) Date: Apr. 6, 2017

(87) PCT Pub. No.: WO2016/054786
PCT Pub. Date: Apr. 14, 2016

(65) Prior Publication Data
US 2017/0333828 A1    Nov. 23, 2017

(51) Int. Cl.
*C07C 7/11* (2006.01)
*B01D 53/04* (2006.01)
(Continued)

(52) U.S. Cl.
CPC .......... *B01D 53/0462* (2013.01); *B01J 20/08* (2013.01); *B01J 20/3433* (2013.01);
(Continued)

(58) Field of Classification Search
None
See application file for complete search history.

(56) References Cited

U.S. PATENT DOCUMENTS

| 3,208,157 A | 9/1965 | Stark |
| 3,211,644 A | 10/1965 | Clark |
| | (Continued) | |

FOREIGN PATENT DOCUMENTS

| CA | 2009332 A1 | 8/1991 |
| DE | 10 2008 007 081 A1 | 8/2009 |
| | (Continued) | |

OTHER PUBLICATIONS

U.S. Appl. No. 15/517,558, filed Apr. 7, 2017, Hans-Guenter Wagner, et al.

(Continued)

*Primary Examiner* — Tam M Nguyen
(74) *Attorney, Agent, or Firm* — Oblon, McClelland, Maier & Neustadt, L.L.P.

(57) ABSTRACT

The invention relates to a process for the regeneration of an adsorber. For the regeneration a liquid stream (S2) comprising at least one alkane is converted from liquid phase into gaseous phase. Then the adsorber is regenerated and heated by contact with gaseous stream (S2) up to 230 to 270° C. Subsequently, the adsorber is cooled first by contact with gaseous stream (S2) to a temperature of 90 to 150° C. followed by cooling with liquid stream (S2) to a temperature below 80° C. The outflow of the adsorber (S2*) during the cooling with gaseous stream (S2) and optionally the outflow of the adsorber (S2*) during cooling with liquid stream (S2) is recycled in at least one of these steps.

22 Claims, 2 Drawing Sheets

Figure 1:
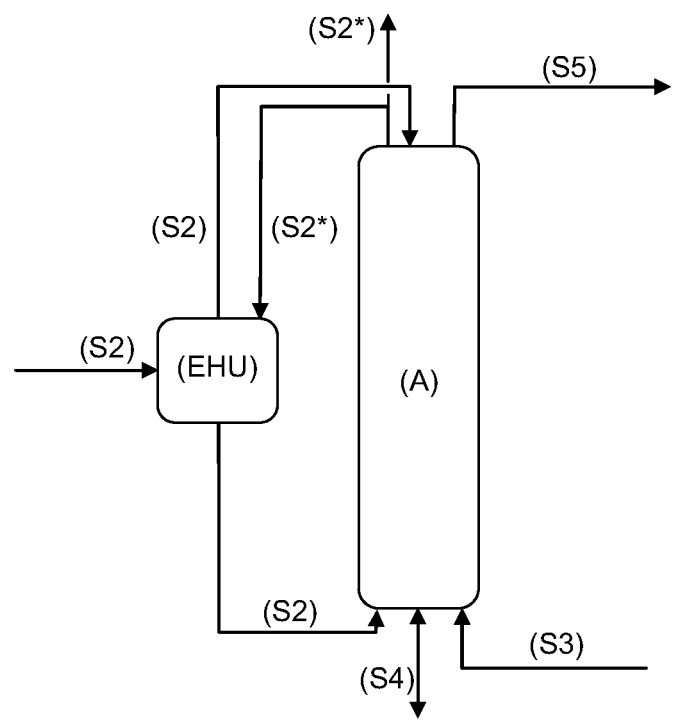

(51) Int. Cl.
  *C10G 25/12* (2006.01)
  *C10G 57/02* (2006.01)
  *C10G 67/06* (2006.01)
  *C10G 69/12* (2006.01)
  *B01J 20/08* (2006.01)
  *B01J 20/34* (2006.01)
  *C10G 25/05* (2006.01)

(52) U.S. Cl.
  CPC ....... *B01J 20/3458* (2013.01); *B01J 20/3483* (2013.01); *C07C 7/11* (2013.01); *C10G 25/05* (2013.01); *C10G 25/12* (2013.01); *C10G 57/02* (2013.01); *C10G 67/06* (2013.01); *C10G 69/126* (2013.01); *B01D 2253/104* (2013.01); *B01D 2256/24* (2013.01); *B01D 2259/40054* (2013.01); *B01D 2259/40067* (2013.01)

(56) References Cited

U.S. PATENT DOCUMENTS

| | | |
|---|---|---|
| 3,725,377 A | 4/1973 | Cottle |
| 4,935,399 A | 6/1990 | Blackburn et al. |
| 4,935,400 A | 6/1990 | Blackburn et al. |
| 5,177,298 A | 1/1993 | Yon et al. |
| 5,510,566 A | 4/1996 | Muoio et al. |
| 6,673,239 B2 | 1/2004 | Johnson et al. |
| 8,557,029 B2 | 10/2013 | Force et al. |
| 2007/0123743 A1 | 5/2007 | Ng et al. |
| 2011/0021851 A1 | 1/2011 | Towler et al. |
| 2011/0301398 A1 | 12/2011 | Heidemann et al. |
| 2012/0024324 A1 | 2/2012 | Force et al. |

FOREIGN PATENT DOCUMENTS

| | | |
|---|---|---|
| EP | 0 229 994 A1 | 7/1987 |
| WO | WO 01/83407 A1 | 11/2001 |
| WO | WO 2005/056503 A1 | 6/2005 |
| WO | WO 2010/057905 A1 | 5/2010 |
| WO | WO 2010/123748 A1 | 10/2010 |

OTHER PUBLICATIONS

U.S. Appl. No. 15/517,848, filed Apr. 7, 2017, Hans-Guenter Wagner, et al.
U.S. Appl. No. 15/517,682, filed Apr. 7, 2017, Hans-Guenter Wagner, et al.
U.S. Appl. No. 15/517,857, filed Apr. 7, 2017, Hans-Guenter Wagner, et al.
U.S. Appl. No. 15/517,695, filed Apr. 7, 2017, Hans-Guenter Wagner, et al.
International Search Report dated Jul. 3, 2015 in PCT/CN2014/088225 (English language translation only).
International Search Report dated Jul. 3, 2015 in PCT/CN2014/088225.
International Preliminary Report on Patentability and Written Opinion dated Apr. 20, 2017 in PCT/CN2014/088225.
Extended European Search Report dated May 22, 2018 in Patent Application No. 14903610.5.

RECYCLING PROCESS FOR ADSORBER REGENERATION

The invention relates to a process for the regeneration of an adsorber. For the regeneration a liquid stream (S2) comprising at least one alkane is converted from liquid phase into gaseous phase. Then the adsorber is regenerated and heated by contact with gaseous stream (S2) up to 230 to 270° C. Subsequently, the adsorber is cooled first by contact with gaseous stream (S2) to a temperature of 90 to 150° C. followed by cooling with liquid stream (S2) to a temperature below 80° C. The outflow of the adsorber (S2*) during the cooling with gaseous stream (S2) and optionally the outflow of the adsorber (S2*) during cooling with liquid stream (S2) is recycled in at least one of these steps.

Technical organic compositions often need to be purified from compounds containing heteroatoms in particular heteroatoms like sulfur or oxygen before use as starting materials in catalyzed reactions. These impurities may inhibit or lower the activities of catalysts. The purification can be performed by employing adsorbers.

WO 2010/057905 A1 discloses a process for the oligomerization of olefins by bringing at least one C2 to C8 olefin into contact with a nickel containing heterogeneous catalyst. Preferably the olefins are passed over an adsorption material before being brought in contact with the catalyst in order to prevent catalyst poisoning. However, WO 2010/057905 A1 does not disclose a process for the regeneration of adsorbers.

DE 10 2008 007 081 A1 discloses a process for the production of n-butene-oligomers and 1-butene from a technical mixture of $C_4$-hydrocarbons. Analogously to WO 2010/057905 A1, the document mentions the need for the removal of certain compounds containing heteroatoms out of the hydrocarbon mixture intended to be used in the catalyzed oligomerization process. The document does not disclose a process for the regeneration of adsorbers.

WO 2005/056503 discloses a composite catalyst for the selective oligomerization of lower alkenes and the production of high octane products. While the oligomerization of lower alkenes and mixtures of alkenes is reported in detail, the use of adsorbers for purification of the starting materials or the regeneration of adsorbers is not mentioned.

WO 01/83407 describes a process for the oligomerization of alkenes having from 3 to 6 carbon atoms using a catalyst containing a zeolite of the MFS structure type under conditions to obtain selectively oligomeric product containing predominant amount of certain oligomers. Like in the previously discussed document of prior art neither the use of adsorbers for purification of starting materials nor their regeneration is part of the disclosure.

In order to remove the adsorbed compounds containing heteroatoms the regeneration of the adsorbers is required periodically. This can be achieved, for example, by purging the adsorber with inert gases or hydrocarbons at elevated temperatures. Suitable regeneration media need to be essentially free of olefins and compounds containing heteroatoms, in particular free of compounds containing oxygen and sulfur. Residual olefins tend to form detrimental coke and polymer precipitates on the adsorbent, at the temperatures applied, during the regeneration process.

Technical organic compositions comprising olefins purified in an adsorber often comprise significant amounts of saturated hydrocarbons. These purified saturated hydrocarbons may be separated from the olefins in downstream process steps and would be applicable for the regeneration of the adsorbers. However, even after distillation of the product stream, the saturated hydrocarbon fraction usually still contains considerable amounts of residual olefins. Streams containing considerable amounts of olefins cannot successfully be employed for adsorber regeneration due to the increased formation of precipitates and/or coke on the adsorber surface.

U.S. Pat. No. 4,935,399 and U.S. Pat. No. 4,935,400 both describe a similar process for the reduction of hydrocarbon losses during regeneration of adsorbers containing molecular sieves for the removal of sulfur compounds from liquid hydrocarbon streams. While the process according to U.S. Pat. No. 4,935,399 comprises heating of the adsorber bed directly by a device located within the adsorber bed, in U.S. Pat. No. 4,935,400 the adsorber bed is heated by purging with gaseous hydrocarbon only. Both documents explain the use of hydrocarbon streams for the regeneration of adsorber beds containing molecular sieves, but none of them deals with the recycling of hydrocarbons recycled in a cooling step.

U.S. Pat. No. 5,177,298 discloses a process for regeneration of oxygenate-containing adsorbents using hydrocarbon regenerant streams. The streams used require extra pretreatment by additional adsorbers in order to remove compounds containing sulfur or oxygen. Furthermore, U.S. Pat. No. 5,177,298 does not disclose cooling with gaseous regeneration media.

U.S. Pat. No. 6,673,239 B2 discloses a system and process for removing water and compounds containing heteroatoms from hydrocarbons and a system and process for regeneration of adsorbents used therein. The regeneration comprises passing an isoparaffin over a water-adsorbent, then passing the isoparaffin over the heteroatom-containing compound adsorbent. However, U.S. Pat. No. 6,673,239 B2, does not deal with the recycling of regeneration media recovered in a cooling step.

US 2012/0024324 A1 discloses a process for regeneration of purification beds with a jet compressor in an open loop cycle. A fluid composition comprising an inert gas and a regeneration composition is used as regeneration media. Apart from hydrogen as possible secondary component, further constituents of the fluid composition are not defined. In particular the application of hydrocarbons as regeneration media is not considered in the disclosure.

The problem underlying the present invention consists in the development of a new process for regeneration of adsorbers.

The object is achieved by a process for the regeneration of an adsorber comprising the steps a) to e):

a) converting a stream (S2) comprising at least one alkane from liquid phase into gaseous phase, b) regenerating the adsorber by contact with gaseous stream (S2) in a range of 230 to 270° C., c) cooling the adsorber by contact with gaseous stream (S2) obtained in step a) to a temperature in a range of 90 to 150° C., d) optionally cooling the adsorber to a temperature below 80° C. by contact with liquid stream (S2) without prior conversion into gaseous phase, e) recycling of the outflow (S2*) of the adsorber as obtained in step c) and/or optionally in step d), wherein the outflow (S2*) is recycled at least partially to at least one of the steps a) to d).

The process according to the present invention allows the recycling and reuse of regeneration media for the regeneration of an adsorber obtained as outflow in the cooling step of the same regeneration process. Consequently, the consumption of regeneration media can be lowered. Furthermore, the regeneration media can also be reused in gaseous state, saving energy for the conversion of the regeneration media from liquid phase into gaseous phase.

When regeneration media is reused in gaseous phase compression of the outflow of the cooling step may be performed by use of jet compressors. These are, in contrast to conventional compressors, robust, simple, need no moveable parts and tolerate varying temperatures and pressures. By using jet compressors, energy already embedded in pressure differences between streams in the assembly can be exploited for compression. Therefore, no extra external energy for compression is consumed in this embodiment.

Hydrocarbons comprising residual olefins, corresponding to stream (S1) within the context of the present invention, can be applied for adsorber regeneration, without significant formation of detrimental precipitates of coke and polymers on the adsorbent. Within the context of the present invention, the stream (S2) is being employed as regeneration stream or regeneration media of an adsorber. In order to hydrogenate residual olefins in stream (S1) to obtain stream (S2), hydrogen gas and suitable catalysts are required. Therefore, lowering the consumption of regeneration medium reduces the amount of stream (S1) to be hydrogenated. By consequence, recurring costs for hydrogen and catalyst regeneration are decreased.

In another embodiment of the present invention, the stream (S1) originates from an earlier process step. Thus, the present invention allows the employment of components as regeneration media for an adsorber whereby said components have been purified earlier on the same adsorber, but who are in fact by-products, for example, within a process for producing octene by dimerization of butene. Such by-products are usually discharged as waste, but within the process of the present invention they can be successfully employed/converted into a regeneration stream.

Compared to other processes of prior art, no additional purification step to remove compounds containing sulfur and oxygen or other heteroatoms is required since these hydrocarbon mixtures are obtained for example as side products during purification of technical organic compositions comprising olefins by means of adsorbers. The purchase of alternative regeneration media like inert gases is therefore avoided.

Furthermore, another advantage of the present invention can be seen in the fact that one embodiment of the invention allows the operation of at least one adsorber in regeneration mode parallel to the operation of at least one other adsorber in operation mode in the same plant.

It is also an advantage that according to another embodiment of the invention it is possible to collect and to recycle residual organic composition remained in the pores of the adsorber after finishing the operation mode to further reduce losses of valuable organic intermediate.

In order to enrich the regeneration media as much as possible with adsorbed compounds containing oxygen and/or sulphur and consequently consuming regeneration media in an amount as low as possible, the flow of the regeneration media can be directed opposite to the flow of any organic composition in the operation mode of the adsorber.

For cooling of the adsorber the regeneration media can be passed through the adsorber according to the direction of the flow of any organic composition during the operation mode taking full advantage of the temperature gradient within the adsorber, further lowering the consumption of regeneration media.

In summary, operating costs and environmental burden are lowered by reduction of energy consumption, waste, recycling of regeneration media and product loss due to a combination of advantageous measures implemented in the present invention. Furthermore, the present invention provides a method for efficient regeneration of adsorbers.

The invention is specified in more detail as follows:

The present invention relates to a process for the regeneration of an adsorber comprising the steps a) to e).

Within the context of the present invention, the term "adsorber" comprises the adsorbent as well as the device in which the adsorbent is embedded in. Instead of the term "adsorbent" the expression "adsorber material" may be used. The term adsorber may be used equivalently for adsorbent, even if a certain statement actually refers only to the adsorbent but not to the device in which the adsorbent is embedded in.

The absorber can be employed for the adsorption of compounds containing oxygen and/or sulphur out of organic compositions. Preferably, the adsorber (A1) can be employed for the adsorption of ethers, alcohols, thiols, thioethers, sulfoxides, ketones, aldehydes or mixtures thereof.

Any adsorbent known to the person skilled in the art being appropriate for performing the adsorption of compounds containing oxygen and/or sulphur out of organic compositions may be applied.

Preferred adsorbents are, for example, molecular sieves with a pore diameter of 4 to 15 Å. Further, molecular sieves applicable are crystalline, natural aluminia silicates, like layer lattice silicates or synthetic molecular sieves. Furthermore, commercially available molecular sieves as sold by the Bayer AG, Dow, Union Carbide, Laporte or Mobil may be used. These molecular sieves can be, for example, zeolithes of the A-, X. and Y-type. Moreover, synthetic molecular sieves comprise silicium and aluminium as main components, whereby other atoms as side-components such as lanthanides like gallium, indium and lanthanum or other elements like nickel, cobalt, copper, zinc or silver may be useful. These can be introduced into the zeolithe for example by means of an ion-exchange with exchangeable cations.

Likewise, synthetic zeolithes can be employed, in which other atoms like boron or phosphorus are incorporated in the layer by co-precipitation.

Further suitable adsorbents are aluminium phosphate, silicium dioxide, kieselgur, titanium dioxide, zirconium dioxide, polymeric adsorbents and mixtures thereof.

The most preferred adsorbent is aluminium oxide, commercially available for example as Selexsorb CDL from BASF.

Preferably the adsorber is based on aluminium oxide and/or the adsorber can be employed for the adsorption of compounds containing oxygen and/or sulphur out of organic compositions, preferably the absorber can be employed for the adsorption of ethers, alcohols, thiols, thioethers, sulfoxides, ketones, aldehydes or mixtures thereof.

Regeneration, in the context of the present invention, means desorption and removal of adsorbed compounds containing oxygen and/or sulfur from the adsorber, in particular from the adsorbent in the adsorber. The inventive process for regeneration of the adsorber may also comprise additional measures/steps necessary, for example, for preparation of the regeneration medium, the adsorber itself for regeneration or for enabling the adsorber after finished regeneration to be operated again for adsorption of compounds containing oxygen and/or sulphur out of organic compositions.

Consequently, an adsorber, within this invention, can at least be operated in the modes of operation: operation mode or regeneration mode.

An adsorber, within this invention, is in operation mode, when a stream comprising an organic composition, comprising at least one alkane and/or at least one olefin and compounds containing oxygen and/or sulfur, preferably not being routed through the adsorber before, is fed into the adsorber and compounds containing oxygen and/or sulfur are adsorbed completely or at least partially from this stream on the adsorbent.

Preferably at least 50%, more preferably at least 80%, most preferably at least 97% of the compounds containing oxygen and/or sulfur are adsorbed from the stream comprising organic composition according to the preceding paragraph.

An adsorber, within this invention, is in regeneration mode when measures to remove or measures related to the removal of adsorbed compounds containing oxygen and/or sulphur from the adsorbent are carried out or optionally the definition of the operation mode does not apply.

The steps a), b), c), d) and e) within the process for regeneration of an adsorber according to the present invention are defined as follows:

In step a) a stream (S2) comprising at least one alkane is converted from liquid phase into gaseous phase.

Preferably the alkane contains 1 to 14, more preferably 3 to 10, most preferably 4 to 6 carbon atoms in its longest chain.

The stream (S2) comprises preferably at least 99 wt-% of at least one alkane, more preferably at least 99.5 wt-% of at least one alkane, most preferably at least 99.9 wt-% of at least one alkane, preferably the alkane is butane.

The at least one alkane can be, for example, linear, branched and/or cyclic and is selected from the group: methane, ethane, propane, butane, pentane, hexane, heptane, octane, nonane and decane. Preferably the at least one alkane is butane.

In the context of the present invention, if not stated otherwise, it is not differentiated between the different isomers of a certain alkane. For example, the term butane may refer to n-butane and/or isobutane.

The stream (S2), stream (S1) and stream (S2*) ((S2*) and (S1) as defined below) may comprise in a specific embodiment one or more further alkanes different from butane, which may be selected from the same alkanes as specified above.

The stream (S2) may comprise not more than 1000 wt-ppm olefin, preferably not more than 500 wt-ppm olefin, most preferably not more than 100 wt-ppm olefin, preferably the olefin is butene.

The olefin in stream (S2), stream (S1), and stream (S2*) ((S1), (S2*) as defined below) may comprise at least one linear, branched, cyclic monoolefin and/or at least one linear, branched, cyclic olefin containing more than one olefinic double bond. Preferably the olefin has 2 to 14, more preferably 3 to 10, most preferably 4 to 6 carbon atoms in its longest carbon chain.

If more than one stereoisomer of an olefin exists, e.g. the corresponding cis- and trans-isomer, these isomers are, in the context of the present invention, regarded as equivalent. Further, it is not differentiated between constitutional isomers of monoolefins. For example, the term butene may comprise the constitutional isomers 1-butene and/or 2-butene as well as 2-butene the corresponding cis- and/or trans-stereoisomer.

Monoolefins can be, for example, selected from the group: ethene, propene, butene pentene, hexene, heptene, octene, nonene and decene. Preferably, the olefin is butene.

If at least one olefin containing more than one olefinic double bond is present, this olefin is preferably a diene, more preferably butadiene.

The stream (S2), stream (S1) and stream (S2*) ((S2*) and (S1) as defined below) may comprise in a specific embodiment one or more further olefins different from butene which may be selected from the same olefins as specified above The conversion of liquid stream (S2) into gaseous phase may be carried out by lowering the pressure and/or heating of the liquid stream (S2), preferably by employing at least one evaporator (EV) and/or at least one super-heater (SH1) and/or at least one flash vessel (FV).

In a preferred embodiment, liquid stream (S2), originating from step e), with a pressure of 5 to 80 bar, preferably of 10 to 50 bar, most preferably of 20 to 30 bar, is, for the conversion according step f), fed into a flash vessel, wherein the pressure of liquid stream (S2) is lowered to 4 to 16 bar, preferably to 7 to 13 bar, most preferably to 8 to 11 bar.

Lowering the pressure of liquid stream (S2), preferably in a flash vessel, compared to the pressure of liquid (S2) obtained in step e), can result in conversion of at least a part of liquid stream (S2) into gaseous phase. Remaining liquid stream (S2) at lowered pressure may be converted into gaseous phase by use of at least one evaporator.

By lowering the pressure of liquid stream (S2), preferably in a flash vessel, compared to the pressure of liquid stream (S2) obtained in step a), 0 to 80%, preferably less than 10% of liquid stream (S2) may be converted into gaseous phase.

Alternatively, liquid stream (S2) may be converted into gaseous phase, preferably with at least one evaporator, without prior lowering the pressure compared to the pressure obtained for stream (S2) in an optional step f) (as defined below).

Within the present invention, an evaporator is a device which converts a liquid stream into gaseous phase by transfer of heat to the liquid stream.

It is also possible to use two or more evaporators through which stream (S2) may flow in series and/or in parallel.

Any evaporator known to the person skilled in the art being appropriate for performing the evaporation may be applied.

Examples for evaporators are electric evaporators and evaporators transferring heat by means of a heat transfer medium, like steam (gaseous water) or other gaseous media, hydrocarbons, oils or salts. Preferably, the evaporators are of the Kettle type.

The conversion of liquid stream (S2) into gaseous phase according to step a) may also comprise super-heating.

Super-heating, in the context of the present invention, means further increasing the temperature of the already gaseous stream (S2), preferably by transfer of heat to the gaseous stream (S2).

Any super-heater known to the person skilled in the art being appropriate for the super-heating may be applied.

Super-heating may be performed with one or more super-heaters. When more than one super-heater is used, the super-heaters can be arranged in series and/or in parallel.

Examples for possible super-heaters are electric super-heaters and super-heaters transferring heat by means of a heat transfer medium, suitable gaseous media, hydrocarbons, oils or salts. Preferably, super-heaters are of the shell-and-tube-type.

Evaporating and super-heating may be performed in different devices and/or be combined in at least one device capable to fulfill both functions, for instance a shell-and-tube heat exchanger stacked on top of a Kettle-type evaporator.

If evaporators and/or super-heaters based on a heat transfer medium are used, the same stream of heat transfer medium may be passed through only one evaporator or super-heater or through more than one evaporator or super-heater. The same stream of heat transfer medium can be used for evaporators or super-heaters or for evaporators and super-heaters.

The same type of heat transfer medium can be applied for all evaporators and/or super-heaters or different types of heat transfer media for each individual device or a group of evaporators and/or super-heaters may be used.

Dependent on the temperature actually required at a given time of the process, the heat transfer to the liquid or gaseous stream (S2) by the respective evaporators and/or super-heaters may be reduced, stopped completely and/or individualor all evaporators and/or super-heaters may be by-passed by stream (S2).

Preferably gaseous stream (S2) is passed through all evaporators and/or super-heaters and heat transfer is reduced or stopped when lower temperatures for gaseous stream (S2) are required.

Preferably evaporators and/or super-heaters are by-passed if liquid stream (S2) is required.

In step b) the adsorber is regenerated by contact with gaseous stream (S2) in a range of 230 to 270° C.

Step b) may comprise at least one of the following component steps b1) to b3):
b1) heating the adsorber by contact with the gaseous stream (S2), wherein the gaseous stream (S2) is condensed within the adsorber,
b2) heating the adsorber by contact with the gaseous stream (S2) up to a temperature in the range of 230 to 270° C. without any condensation of the gaseous stream (S2) within the adsorber,
b3) regeneration of the absorber at a temperature in the range of 230 to 270° C. by contact with the gaseous stream (S2) and/or
wherein cooling in step d) (as defined below) lowers the temperature of the adsorber to 40 to 60° C.

Preferably step g) (as defined below) is carried out prior to step b) and step e) (as defined below) is carried out at the same time as step c) (as defined below), optionally as step d) (as defined below) and step b) comprises the component steps b1), followed by b2), followed by b3), followed by step c), followed by step d).

Condensation, meaning conversion from gaseous into liquid phase, of the components comprised in stream (S2) in step b), in particular in step b1), usually takes place if at least one spot, meaning spacial element, inside the adsorber, being the adsorbent and/or the adsorber wall, has a temperature, which is below the dew point temperature of the respective components comprised in gaseous stream (S2) present at that spot.

The pressure in the adsorber, being in regeneration mode, is defined by the pressure of stream (S2) in the adsorber.

The pressure of stream (S2) in the adsorber may be identical or lower as the pressure of stream (S2) as obtained in step a) and/or, if carried out, f).

In one embodiment of the invention the adsorber to be regenerated in step b) and to be cooled in step c) and/or d) is part of an assembly which contains at least one further adsorber, preferably the at least one further adsorber is in its operation mode during the regeneration of the first adsorber, and/or each adsorber within this assembly is identical in respect of the adsorber material and/or its modes of operation.

Preferably, the recycled outflow according to step e), in the embodiment as specified in the preceding paragraph, of one adsorber can be reused in at least one of the steps a) to e) for the same adsorber or the at least one further adsorber.

Subsequent to step b), the outflow obtained from the absorber, comprising gaseous stream (S2) and the impurities removed from the adsorber may be condensed at least partially, preferably by employing at least one condenser and/or at least one cooler.

Preferably at least 70%, more preferably at least 80% most preferably at least 90% of the outflow obtained from the absorber, comprising gaseous stream (S2) and the impurities removed from the adsorber are condensed.

In a further embodiment the process according to the present invention comprises at least one, preferably all of the options i) to iii) as follows:
i) the heating rate of the adsorber does not exceed 60° C./h, preferably it does not exceed 40° C./h, and/or
ii) the temperature of the gaseous stream (S2) is not more than 100° C., preferably not more than 60° C., higher than the adsorber, especially during the heating steps b1) and/or b2), and/or
iii) the temperature of the gaseous or optionally liquid stream (S2) is not more than 100° C., preferably not more than 60° C., lower than the adsorber, especially during the cooling steps c) and/or d) (steps c and d) as defined below).

In step c) the adsorber is cooled by contact with gaseous stream (S2) obtained in step a) to a temperature in a range of 90 to 150° C.

In an optional step d) the adsorber is cooled to a temperature below 80° C. by contact with liquid stream (S2) without prior conversion into gaseous phase.

After finishing the regeneration of the adsorber according to step d), the adsorber may be switched into its operation mode by feeding it with an organic composition to be purified.

In step e) the outflow (S2*) of the adsorber as obtained in step c) is recycled and/or optionally in step d), wherein the outflow (S2*) is recycled at least partially to at least one of the steps a) to d).

Preferably at least 10%, more preferably at least 25%, most preferably at least 50% of the outflow (S2*) is recycled to at least one of the steps a) to d).

In step e), the outflow (S2*) may comprise >99.5 wt-% of the stream (S2), preferably the outflow (S2*) comprises 100 wt-% of the stream (S2).

(S2*) being recycled to at least one of the steps a) to d) means (S2*) is used in the respective step in the same manner as (S2).

In a further embodiment the outflow (S2*) obtained from the adsorber in step e) is
i) condensed by at least one condenser and/or cooler to obtain a liquid outflow (S2*) and at least partially recycled for being reused as liquid stream (S2) in at least one of the steps a) or d) and/or
ii) compressed, when still in gaseous phase, by at least one compressor to obtain a gaseous outflow (S2*) and at least partially recycled for being reused as gaseous stream (S2) in at least one of the steps b) or c), preferably without prior evaporation in an evaporator or routing through at least one flash vessel or through at least one evaporator.

Any condenser and/or cooler known to the person skilled in the art being appropriate for performing the condensation may be applied for condensation of the outflow (S2*).

Any compressor known to the person skilled in the art being appropriate for performing the compression may be applied for compression of the outflow (S2*).

Preferably at least one compressor is a jet compressor and/or i) preferably, the stream (S2) fed into the jet compressor has a pressure of 10 to 40 bar, more preferably 20 to 30 bar, and/or ii) the pressure of stream (S2) fed into the jet compressor is 5 to 30 bar higher, preferably 10 to 20 bar higher than the pressure of the outflow of the jet compressor, and/or iii) the pressure of stream (S2) fed upstream into a flash vessel and the pressure of the outflow of the flash vessel, comprising stream (S2), is 10 to 40 bar, preferably 20 to 30 bar.

The inventive process may comprise an additional step f), carried out prior to step a) wherein stream (S1) comprising at least one alkane and at least one olefin, is hydrogenated, to obtain a liquid stream (S2) comprising at least one alkane and a reduced amount of at least one olefin compared to the amount of stream (S1).

Preferably step a) is followed by step b), step is followed by step c), step c) is followed by step d) and step d) followed by step e).

In step f), the stream (S1) may comprise butane and butene, preferably at least 96 wt-% butane and not more than 4 wt-% butene.

The stream (S1) may comprise at least one alkane and at least one olefin in a total of at least 99 wt-%, more preferably in a total of at least 99.5 wt-%, most preferably in a total of at least 99.9 wt-%.

In another embodiment of the invention the stream (S1) originates from the organic composition which has been purified earlier by the same adsorber or by a similar further adsorber during the operation mode of the respective adsorber.

Preferably in the embodiment as specified in the preceding paragraph, an oligomerization of olefins, preferably a dimerization of butene to octene, and/or a distillation step to separate butane from butene is carried out prior to step f) and after the purification of the organic composition employing at least one adsorber in its operation mode.

In a further embodiment the process according to the present invention comprises at least one, preferably all of the options i) to iv) as follows:

i) prior to carrying out step b) a draining step g) is carried out in order to at least partially remove an organic composition which was passed through the adsorber during its operation mode, optionally the organic composition obtained in the draining step g) is collected in a device, preferably in a buffer vessel, in order to pass the collected condensate through an adsorber during its operation mode, and/or ii) condensate obtained in step b) comprising the stream (S2) and the residue of the organic composition which was not removed from the adsorber when carrying out draining step g), is collected in a device, preferably in buffer vessel, in order to pass the collected condensate through an adsorber during its operation mode.

Preferably at least 10 wt-%, more preferably at least 30 wt-%, most preferably at least 40 wt-% of the organic composition is removed during the draining step g).

The Organic composition usually comprises at least one olefin, at least one alkane and optionally at least one compound containing oxygen and/or sulphur.

The organic composition comprises preferably at most 80 wt-%, more preferably at most 70 wt-%, most preferably at most 50 wt-% of at least one alkane. Preferably the at least one alkane is butane.

Further, the organic composition comprises preferably at least 19 wt-%, more preferably at least 29 wt-%, most preferably at least 49 wt-% of at least one olefin. Preferably the at least one olefin is butene.

Organic composition passed through the adsorber and/or obtained in the draining step g) and/or being part of the condensate obtained in step b) comprises preferably not more than 1000 wt-ppm of compounds containing oxygen and/or sulphur.

The organic composition comprises preferably not more than 1.0 wt-% of dienes, preferably butadiene.

In a further embodiment the process according to the present invention comprises at least one, preferably all of the options i) to iv) as follows:

i) in step f), the stream (S1) comprises butane and butene, preferably at least 96 wt-% butane and not more than 4 wt-% butene, and/or ii) the stream (S2) comprises not more than 1000 wt-ppm olefin, preferably not more than 500 wt-ppm olefin, most preferably not more than 100 wt-ppm olefin, preferably the olefin is butene, and/or iii) the stream (S2) comprises at least 99 wt-% of at least one alkane, preferably at least 99.5 wt-% of at least one alkane, most preferably at least 99.9 wt-% of at least one alkane, preferably the alkane is butane and/or iv) in step e), the outflow (S2*) comprises >99.5 wt-% of the stream (S2), preferably the outflow (S2*) comprises 100 wt-% of the stream (S2) and/or v) at least 10%, preferably at least 25%, most preferably at least 50% of the outflow (S2*) is recycled to at least one of the steps a) to d).

FIGURES

The FIGS. 1 to 4 illustrate certain aspects of the invention. For the sake of clarity not all applicable components and embodiments are drawn in one and/or all figures. Embodiments shown in different figures may be combined with each other and do not exclude the incorporation of further components within the limits of the disclosure of the specification.

FIG. 1 illustrates the most basic assembly of the present invention. The stream (S2) is routed through the evaporation/heating unit (EHU) in order to be converted from the liquid into gaseous phase. Then the adsorber (A) is regenerated by contact with gaseous stream (S2) coming from the evaporation/heating unit (EHU) fed into the adsorber in opposite direction to the direction of flow of the stream (S3). The stream (S3) comprises organic composition and compounds containing heteroatoms. The stream (S5) comprises organic composition and no compounds containing heteroatoms or a lower amount of compounds containing heteroatoms than stream (S3). Stream (S5) is leaving adsorber (A) on the opposite end of adsorber (A), chosen for the introduction of stream (S3) into the adsorber (A). The streams (S3) and (S5) are only present during operation mode.

The stream (S4) comprises at least the stream (S2) and/or compounds containing oxygen and/or sulfur. The stream (S4) is leaving the adsorber (A) during regeneration mode, in regeneration step b) of the process of the present invention, but not during operation mode of the adsorber (A). Stream (S4) may leave the adsorber according to or opposite to the direction of flow of stream (S3). Preferably stream (S4) leaves the adsorber during the steps b), b1), b2) and/or b3) opposite to the direction of flow of stream (S3) and/or during the steps c) and/or d) according to the direction of flow of stream (S3). Stream (S4) may additionally comprise (compared to stream (S2)) those elements (such as compounds containing oxygen and/or sulphur) which were adsorbed by the adsorber from stream (OC2) during its operation mode. (OC2) comprises at least one olefin and/or at least one alkane and at least one compound containing oxygen and/or sulphur.

For cooling of the adsorber, stream (S2) coming from the evaporation/heating unit (EHU) is passed according to the direction of flow of stream (S3) through the adsorber. The stream (S2*) leaving the adsorber during this step is at least partially routed back to the evaporation/heating unit (EHU) for reuse.

Figure 2:
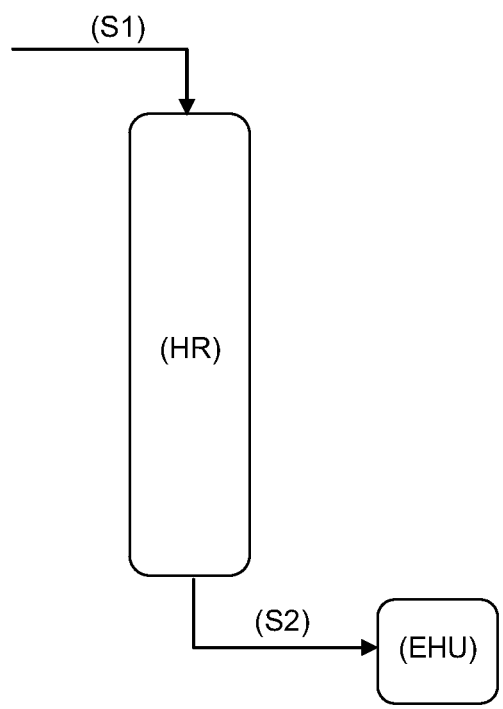

FIG. 2 demonstrates one possible embodiment, in which liquid stream (S2) is obtained by hydrogenation of stream (S1). The stream (S1) is fed into a hydrogenation reactor (HR). The outflow comprises liquid stream (S2) which is routed to the evaporation/heating unit (EHU).

Figure 3:
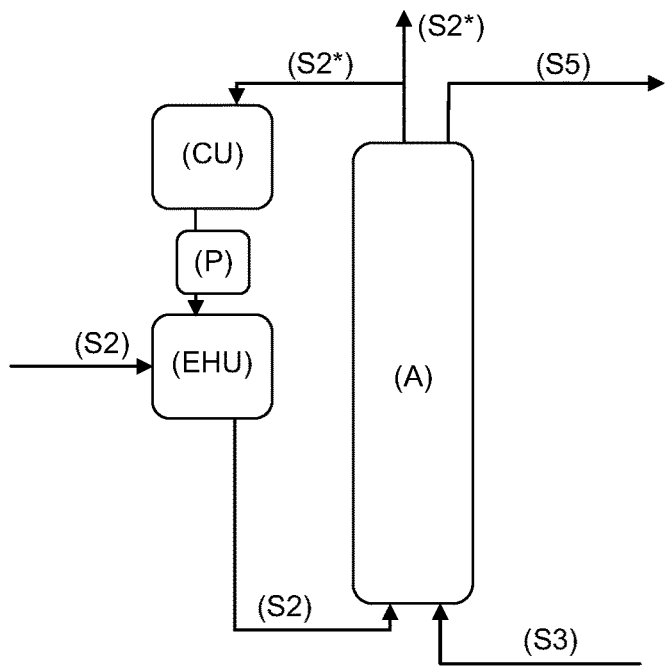

In FIG. 3 one embodiment for the recirculation of liquid or gaseous stream (S2) for reuse is displayed in more detail; gaseous or liquid stream (S2) coming from heating/evaporation unit (EHU) is fed during cooling step d) according to the direction of flow of stream (S3) into the adsorber. The liquid or gaseous stream (S2) leaving the adsorber during cooling step d) is passed through a cooling unit (CU) and routed back to the evaporation/heating unit (EHU) by a pump (P). Cooling unit (CU) comprises at least one cooler and/or condenser which are serially connected and/or parallel-connected with each other.

Figure 4:
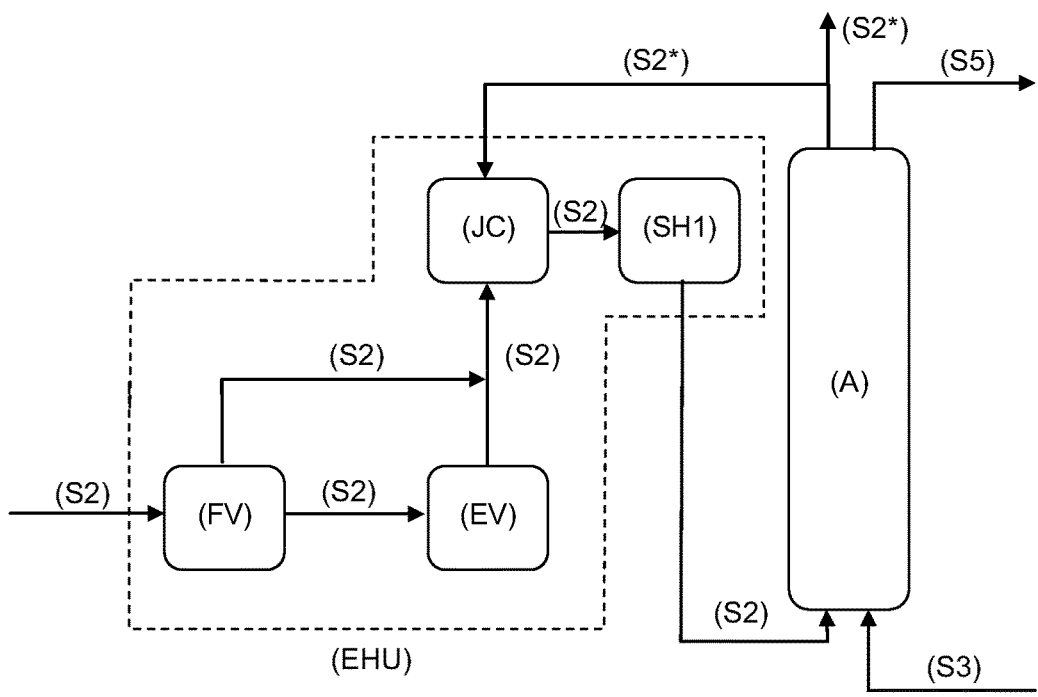

FIG. 4 shows a further alternative embodiment for the recirculation of gaseous stream (S2*). Instead of condensing the outflow of the adsorber (S2*) before reuse, it is routed to the evaporation/heating unit (EHU), comprising additionally a jet compressor (JC). Gaseous stream (S2*) is directly connected with the (EHU) over a jet compressor (JC). From the jet compressor (JC) the stream (S2) is routed via a super heater (SH1) to the adsorber (A). Furthermore, one possible embodiment for the evaporation/heating unit (EHU) is shown in more detail. Liquid stream (S2) is fed into a flash vessel (FV) and routed from there directly and/or indirectly over an evaporator (EV) to the jet compressor (JC). The pressure of liquid stream (S2) provides the energy for the compression of gaseous stream (S2*), if a jet compressor (JC) is applied. However, in embodiments where no jet compressor (JC) or other compressor is incorporated in the assembly, stream (S2) may be passed, coming from the flash vessel (FV) or the evaporator (EV), directly to the super heater (SH1).

The invention claimed is:

1. A process for regenerating an adsorber, the process comprising:
    a) converting a liquid stream ($S2_l$) comprising at least one alkane from liquid phase into gaseous phase, to obtain a gaseous stream ($S2_g$);
    b) regenerating an adsorber by contacting the adsorber with the gaseous stream ($S2_g$) in a range of 230 to 270° C.;
    c) cooling the adsorber by contacting the adsorber with a portion of the gaseous stream ($S2_g$) obtained in a) to a temperature in a range of 90 to 15° C.;
    d) optionally cooling the adsorber to a temperature below 80° C. by contacting the adsorber with the liquid stream ($S2_l$) without prior conversion into gaseous phase; and
    e) recycling an outflow (S2*) of the adsorber as obtained in c) or optionally in d), wherein the outflow (S2*) is at least partially recycled to at least one of a) to d).

2. The process according to claim 1, further comprising, prior to a):
    f) hydrogenating a stream (S1) comprising at least one alkane and at least one olefin, to obtain the liquid stream ($S2_l$) comprising at least one alkane and a reduced amount of at least one olefin compared to an amount of olefin in the stream (S1).

3. The process according to claim 2, wherein:
    i) in f), the stream (S1) comprises butane and butene;
    ii) the liquid stream ($S2_l$) comprises not more than 1000 wt-ppm olefin;
    iii) the liquid stream ($S2_l$) comprises at least 99 wt-% of at least one alkane;
    iv) in e), the outflow (S2*) comprises >99.5 wt-% of the stream (S2); or
    v) at least 10% of the outflow (S2*) is recycled to at least one of a) to d).

4. The process according to claim 3, wherein:
    i) in f), the stream (S1) comprises at least 96 wt-% butane and not more than 4 wt-% butene; or
    ii) the liquid stream ($S2_l$) comprises at least 99 wt-% of butane.

5. The process according to claim 2, further comprising:
    purifying an organic composition with the adsorber or by a similar further adsorber during an operation mode of the adsorber or the similar further adsorber.

6. The process according to claim 5, further comprising, after purifying the organic composition and prior to f):
    oligomerizing olefins; or
    distilling butane from butene.

7. The process according to claim 6, wherein the oligomerizing is carried out and is a dimerization of butene to octene.

8. The process according to claim 1, further comprising
    g) prior to b), at least partially removing an organic composition which was passed through the adsorber during its operation mode, by draining the organic composition, and optionally collecting the drained organic composition in a device, in order to pass the collected condensate through an adsorber during its operation mode; and
    optionally collecting a condensate obtained in b) and comprising the at least one alkane and a residue of the organic composition which was not removed from the adsorber when carrying out g), in a device, in order to pass the collected condensate through an adsorber during its operation mode.

9. The process according to claim 1, wherein the outflow (S2*) obtained from the adsorber in e) is:
    i) condensed by at least one condenser or cooler, to obtain a liquid outflow ($S2_l$*) and at least partially recycled for reuse as liquid stream ($S2_l$) in at least one of a) or d); or
    ii) compressed, when still in gaseous phase, by at least one compressor to obtain a gaseous outflow ($S2_g$*) and at least partially recycled for reuse as gaseous stream ($S2_g$) in at least one of b) or c).

10. The process according to claim 1, wherein the outflow (S2*) obtained from the adsorber in e) is compressed, when still in gaseous phase, by at least one compressor to obtain a gaseous outflow ($S2_g$*) and at least partially recycled for reuse as gaseous stream ($S2_g$) in at least one of b) or c) without prior evaporation in an evaporator or routing through at least one flash vessel.

11. The process according to claim 9, wherein the outflow (S2*) obtained from the adsorber is compressed to obtain the gaseous outflow ($S2_g^*$) and the at least one compressor is a jet compressor, and wherein:
- i) the outflow (S2*) fed into the jet compressor has a pressure of 10 to 40 bar;
- ii) a pressure of the outflow (S2*) fed into the jet compressor is 5 to 30 bar higher, than a pressure of an outflow of the jet compressor; or
- iii) a pressure of the outflow (S2') fed upstream into a flash vessel and a pressure of an outflow of the flash vessel comprising the outflow (S2*) is 10 to 40 bar.

12. The process according to claim 1, wherein the regenerating b) comprises at least one selected from the group consisting of b1), b2), and b3):
- b1) heating the adsorber by contacting the adsorber with the gaseous stream ($S2_g$), wherein the gaseous stream ($S2_g$) is condensed within the adsorber;
- b2) heating the adsorber by contacting the adsorber with the gaseous stream ($S2_g$) up to a temperature in the range of 230 to 270° C. without any condensation of the gaseous stream ($S2_g$) within the adsorber;
- b3) regenerating the adsorber at a temperature in the range of 230 to 270° C. by contacting the adsorber with the gaseous stream ($S2_g$), or wherein the cooling in d) is carried out and lowers the temperature of the adsorber to 40 to 60° C.

13. The process according to claim 12, further comprising:
- g) at least partially removing an organic composition which was passed through the adsorber during its operation mode, by draining the organic composition, wherein g) is carried out prior to b), wherein e) is carried out at the same time as c) and optionally d), wherein b) comprises b1), followed by b2), followed by b3), wherein b) is followed by c), and wherein c) is followed by d).

14. The process according to claim 1, wherein the adsorber comprises an adsorbent based on aluminium oxide or the adsorber is configured to adsorb compounds comprising oxygen or sulphur out of organic compositions.

15. The process according to claim 14, wherein the adsorber is configured to adsorb ethers, alcohols, thiols, thioethers, sulfoxides, ketones, aldehydes, or mixtures thereof.

16. The process according to claim 1, wherein the converting in a) is carried out by heating the liquid stream ($S2_l$).

17. The process according to claim 16, wherein the heating is carried out by employing at least one evaporator, at least one super-heater, or at least one flash vessel.

18. The process according to claim 1, wherein:
- i) a heating rate of the adsorber does not exceed 60° C./h;
- ii) a temperature of the gaseous stream ($S2_g$) is not more than 100° C. higher than a temperature of the adsorber; or
- iii) a temperature of the gaseous stream ($S2_g$) in the cooling c) or the liquid stream ($S2_l$) in the cooling d) is not more than 100° C. lower than a temperature of the adsorber.

19. The process according to claim 1, wherein
- i) subsequent to b), the outflow (S*) obtained from the adsorber comprises the gaseous stream ($S2_g$) and impurities removed from the adsorber, and the outflow (S*) is at least partially condensed; or
- ii) performing the cooling d) and after regenerating the adsorber with d), the adsorber is switched into its operation mode by feeding the adsorber with an organic composition to be purified.

20. The process according to claim 1, wherein the adsorber to be regenerated in b) and to be cooled in c) or d) is part of an assembly that comprises at least one further adsorber.

21. The process according to claim 20, wherein the at least one further adsorber is in its operation mode during the regeneration of the adsorber, or each adsorber within this assembly is identical in respect of their adsorber material or their modes of operation.

22. The process according to claim 20, wherein recycled outflow from the adsorber in e) is reused in at least one of a) to e) for the adsorber or the at least one further adsorber.

* * * * *

UNITED STATES PATENT AND TRADEMARK OFFICE
CERTIFICATE OF CORRECTION

PATENT NO. : 10,137,400 B2
APPLICATION NO. : 15/517286
DATED : November 27, 2018
INVENTOR(S) : Hans-Guenter Wagner et al.

Page 1 of 1

It is certified that error appears in the above-identified patent and that said Letters Patent is hereby corrected as shown below:

In the Specification

In Column 7, Lines 19-20, delete "individualor" and insert -- individual or --, therefor.

In the Claims

In Column 11, Line 64, Claim 1, delete "15°" and insert -- 150° --, therefor.

In Column 13, Line 11, Claim 11, delete "(S2')" and insert -- (S2*) --, therefor.

In Column 14, Line 20 (approx.), Claim 19, delete "wherein" and insert -- wherein: --, therefor.

Signed and Sealed this
Twenty-first Day of April, 2020

Andrei Iancu
*Director of the United States Patent and Trademark Office*